(12) United States Patent
Pavini

(10) Patent No.: US 11,660,412 B2
(45) Date of Patent: May 30, 2023

(54) ENDOTRACHEAL TUBE GUARD WITH OPTIONAL HOLDING SYSTEM AND OPTIONAL SENSOR

(71) Applicant: Marie Pavini, Chittenden, VT (US)

(72) Inventor: Marie Pavini, Chittenden, VT (US)

( * ) Notice: Subject to any disclaimer, the term of this patent is extended or adjusted under 35 U.S.C. 154(b) by 516 days.

(21) Appl. No.: 16/956,870

(22) PCT Filed: Dec. 7, 2018

(86) PCT No.: PCT/US2018/064603
§ 371 (c)(1),
(2) Date: Jun. 22, 2020

(87) PCT Pub. No.: WO2019/113536
PCT Pub. Date: Jun. 13, 2019

(65) Prior Publication Data
US 2021/0052841 A1 Feb. 25, 2021

Related U.S. Application Data

(60) Provisional application No. 62/595,778, filed on Dec. 7, 2017.

(51) Int. Cl.
*A61M 16/04* (2006.01)
*A61M 16/00* (2006.01)

(52) U.S. Cl.
CPC .... *A61M 16/0497* (2013.01); *A61M 16/0003* (2014.02); *A61M 16/0051* (2013.01); *A61M 16/049* (2014.02); *A61M 16/0463* (2013.01); *A61M 2205/13* (2013.01)

(58) Field of Classification Search
CPC .......... A61M 16/0488; A61M 16/0493; A61M 16/049; A61M 16/0461; A61M 16/0497; A61M 16/0683; A61M 16/0003; A61M 16/0051; A61M 16/0463; A61M 2205/13; A61M 2205/18; A61M 2205/276; A61M 2205/332; A61M 16/04–0429
See application file for complete search history.

(56) References Cited

U.S. PATENT DOCUMENTS

| 5,647,358 A | 7/1997 | Vilasi |
| 2007/0113855 A1* | 5/2007 | Carlsen ............. A61M 16/0463 604/243 |
| 2008/0041391 A1 | 2/2008 | Worley |
| 2008/0156322 A1 | 7/2008 | Isenberg et al. |

(Continued)

OTHER PUBLICATIONS

International Search Report and Written Opinion dated Mar. 13, 2019 in connection with PCT/US2018/064603, filed Dec. 7, 2018.

*Primary Examiner* — Elliot S Ruddie
(74) *Attorney, Agent, or Firm* — Downs Rachlin Martin PLLC

(57) ABSTRACT

Disclosed embodiments of an endotracheal tube (ETT) guard system help to hinder self-extubation of the ETT of an awake patient who may reflexively attempt removal, but also allow early mobilization and exercise necessary for preservation of muscle strength. Embodiments may include an ETT holder, which may be generic ETT holders offered by various medical device companies, or a specially configured ETT holder as described herein. Embodiments also may include a sensor that alarms when the ETT guard is moved beyond pre-set motion thresholds.

14 Claims, 6 Drawing Sheets

(56) References Cited

U.S. PATENT DOCUMENTS

2014/0018615 A1\* 1/2014 Lee .................... A61B 1/00165
  600/103
2014/0261441 A1 9/2014 Phillips et al.
2016/0279367 A1\* 9/2016 Kanowitz ......... A61M 16/0497

\* cited by examiner

ENDOTRACHEAL TUBE GUARD WITH OPTIONAL HOLDING SYSTEM AND OPTIONAL SENSOR

FIELD OF THE INVENTION

The present invention generally relates to the field of medical protective systems and protective restraints. In particular, the present invention is directed to endotracheal tube guards and related holding systems and sensors.

BACKGROUND

Despite ETT (endotracheal tube) holders which are designed to secure the ETT to the head of an intubated patient, self-extubations (removal of the ETT) are still possible, not uncommon and can have dire consequences. Patients intubated with an ETT are typically restrained by the wrists and sedated in order to prevent self-extubation, and are thus rendered unable to engage in key elements of reducing morbidity and mortality such as early mobilization in the form of autonomous in-bed activity, and sedation minimization to reduce hallucinations and cognitive decline, both of which have been shown to improve quality of life after intubation, and prevent PICS (post-intensive care syndrome), a form of PTSD (post-traumatic stress disorder). Often in a state of confusion either from illness, medication, or sleep, patients reach to remove the ETT from their mouths. Prevention of self-extubation with restraint and sedation is necessary as inopportune removal of the ETT can lead to respiratory failure and death and nurses are not always with patients to prevent this event.

As shown, for example, in FIG. 1 typical features of an ETT system include external tube 10, and internal tube 12 with a cuff 14 positioned proximally for seating in the patient's airway. ETT holder 15 may include a mouthpiece or lip protector 16 and tube clamp 18 such as locking clamp 20 to secure the ETT through and in ETT holder 15. Other components of an ETT system may include attachment/inflation port 24 communicating with balloon cuff 14 via cuff tubing 44, multi-port connector 26 attachable through adjustable fitment 22, vent tube port 28 and expandable vent tube 30, bronchoscopy port 32 and lock 34, suction port 36 and suction catheter 38. The ETT holder may be secured in the patient's mouth using a head strap 40. Cheek protectors 42 prevent excessive rubbing on the patient's cheek.

Various types of ETT holders are employed in an attempt to secure the ETT to the patient's mouth and head. However, existing systems do not provide reliable or sufficient protection from self-extubation. Difficulties with existing systems can burden the ICU staff, who may be required to spend more time watching one patient to the detriment of another and to their documentation and medication dispersal duties.

SUMMARY OF THE DISCLOSURE

Disclosed embodiments help to hinder self-extubation of the ETT of an awake patient who may reflexively attempt removal, but also allow early mobilization and exercise necessary for preservation of as much muscle strength as possible, promotion of diaphragmatic motion necessary for liberation from the ventilator and reduction of patient stress from not being tied to the bed, allowing for sedation minimization and improved cognition. Embodiments may include an ETT holder be utilized without the ETT holder, or attached to any ETT holder currently on the market. Embodiments may also include a sensor that alarms when the ETT guard tube is pulled.

Disclosed embodiments may be made from conventional and readily available, medically-approved materials such as sensors, cottons, and plastics, which are transparent, latex free, MRI and other diagnostic modality-friendly, potentially disposable, lightweight, quickly and easily attachable and detachable, sturdy, and cleanable. The ETT guard tube encases the ETT, but does not touch it. The proximal end of the ETT guard tube is at the distal end of the lip protector of the ETT holder and the distal end is at the proximal portion of the multiport locking mechanism of the ventilator connector system. The ETT guard tube may have a telescoping mechanism or other longitudinal expansion mechanism within the body of the tube for length adjustability. The proximal straps are rigid and attach within the head straps of the ETT holder system. The distal straps are flexible and also attach to the head straps of the ETT holder system. The portion of the ETT guard tube distal to the rigid straps and proximal to the flexible straps is resiliently expandable or stretchable in a longitudinal direction when pulled distally and returning to its collapsed form when released. A sensor may be placed on the ETT guard tube to indicate an alarm when the tube is squeezed, extended or otherwise moved. At the proximal and distal ends of the ETT guard tube on the side that the side port of the ventilator connector system extends outward, are securement points which open and close/lock the ETT guard tube. On that side is a longitudinal opening from one securement point to the other with width measurements greater than the width of the ventilator connector system. The ETT guard tube has a greater diameter than that of the ventilator connector system and may have different diameters from proximal to distal ends. The ETT guard tube may be reconfigured to accommodate various commercially available multi-port connector systems.

Embodiments of the systems disclosed may include an ETT holder system to include a tube clamp with locking mechanism, mouth piece, lip protector, cheek protectors and padded head straps with hook and loop fasteners, in continuity. The ETT holder system may also include an annular connector on the mouth piece portion for direct and secure connection to the ETT guard tube, which may eliminate the need for the rigid and flexible straps between the ETT holder and ETT guard tube.

In one example of the disclosed embodiments, a medical staff person places the ETT guard tube around the ETT system after intubation at the lengthwise opening assuring that the ventilator port of the distal ETT system protrudes from that opening. The length of the ETT guard tube is adjusted using the telescoping mechanism. The ETT guard tube is locked in place using the securement mechanisms.

As may be apparent to persons of ordinary skill, the embodiment of the disclosed system allows distal pulling on the ETT guard tube without dislodgement of the ETT system which prevents the awake and so-inclined subject from dislodging the ETT system. Other advantages of the disclosed system include providing a safe level of freedom and exercise while preventing self-extubation by a confused or inattentive patient.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 8 and 9 are perspective views of a further alternative embodiment of a guard tube, wherein FIG. 8 shows the guard in a closed position and FIG. 9 shows the guard in an open position.

DETAILED DESCRIPTION

Embodiments enclosed herein offer an ETT guard with or without an ETT holder as part of a complete system, thereby allowing touching and pulling on the ETT guard without moving the ETT encased within it and may include a sensor that alarms when the device is pulled upon. Persons of ordinary skill will note that while the description of embodiments herein is made primarily with reference to ETTs, embodiments and teachings herein are equally applicable with other orally or nasally placed patient access tubes.

Figure 1:
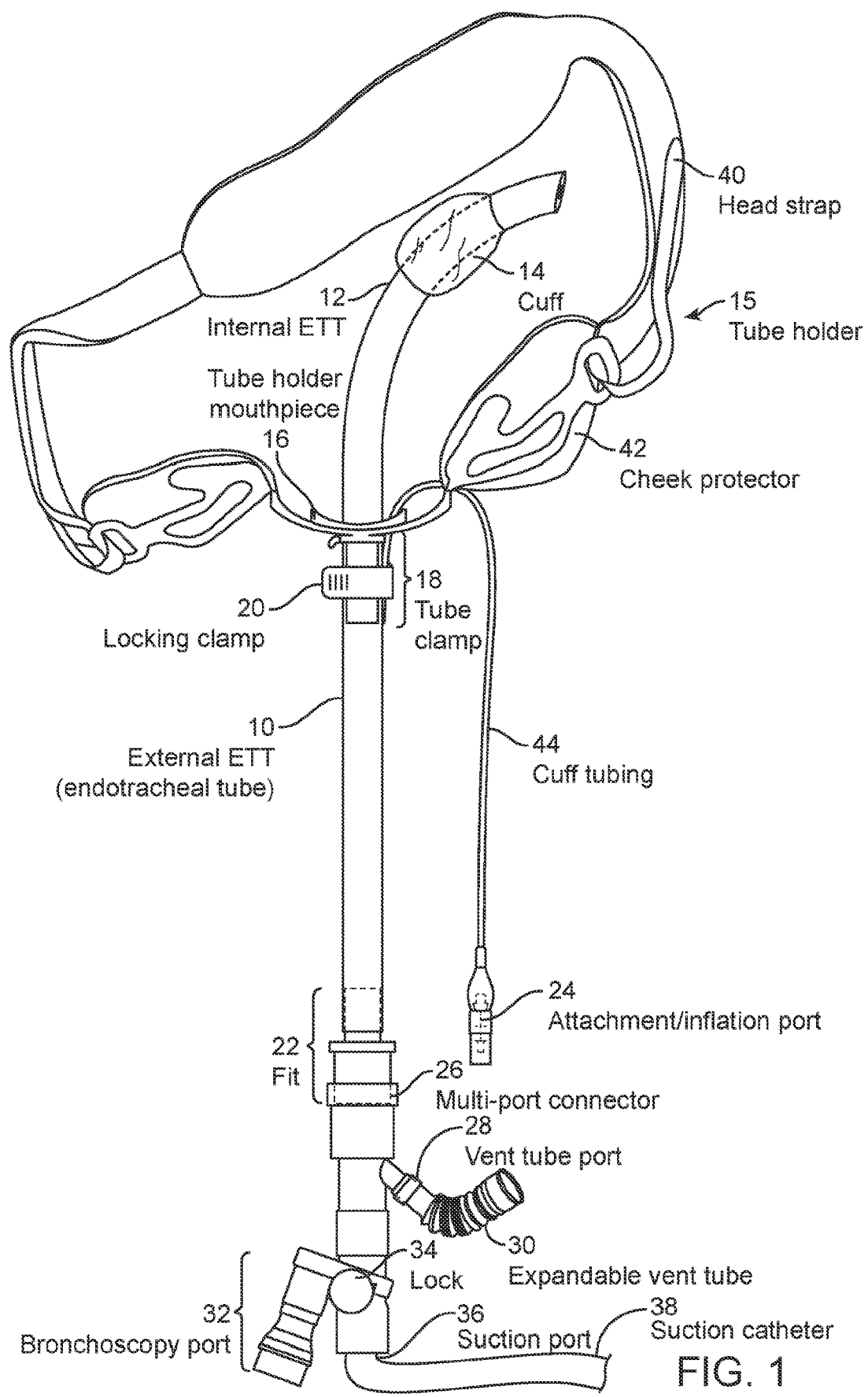
FIG. 1 is an elevation view of an ETT system including ETT, ETT holder system (proximal) and ventilator connector system (distal).
Figure 2:
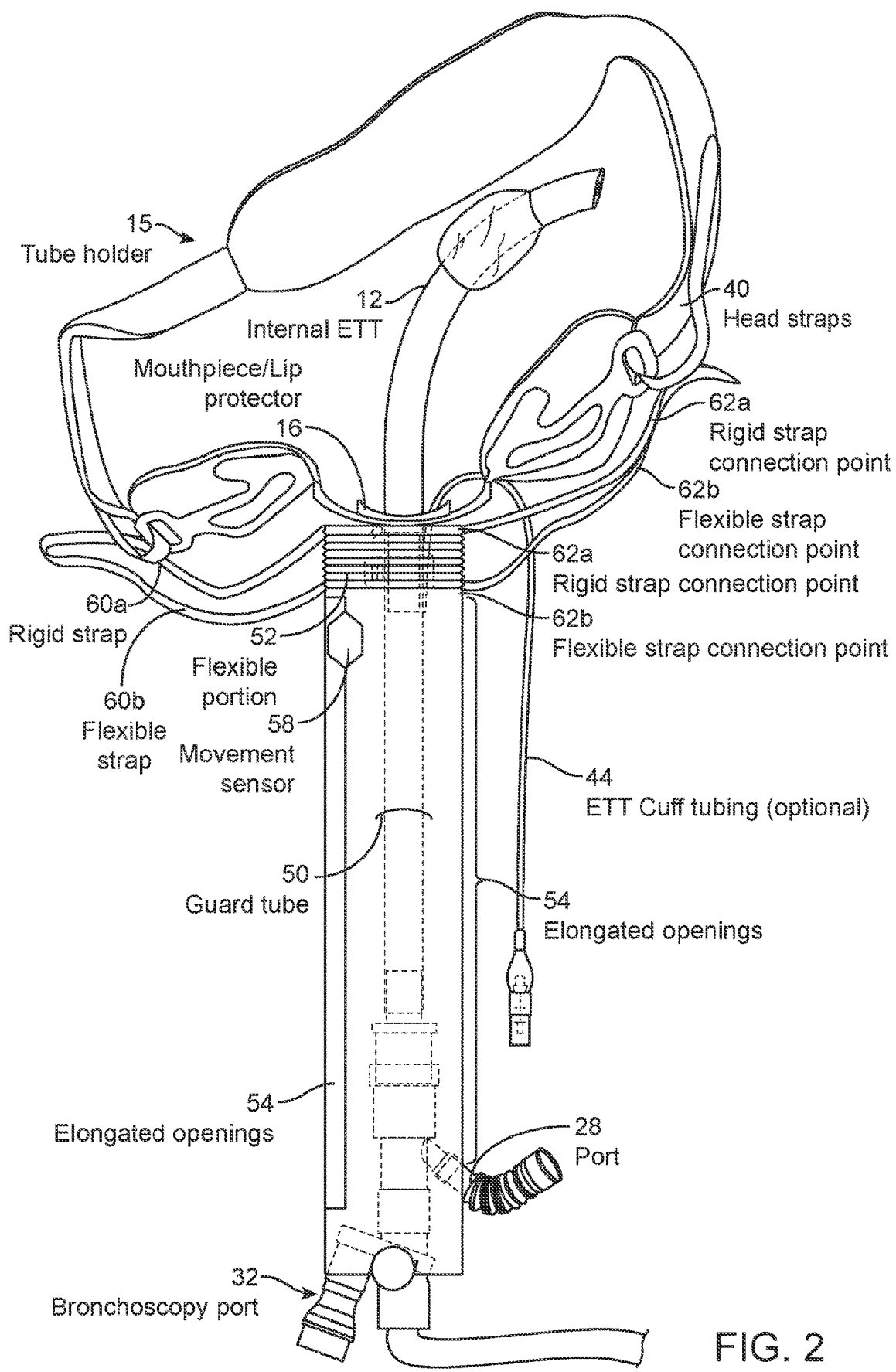
FIG. 2 is an elevation view of an ETT guard tube according to an embodiment of the present disclosure, placed over an ETT system as shown in FIG. 1.

As shown in FIG. 2, an embodiment of an ETT guard as disclosed herein may include guard tube 50 formed as an elongate tube structure configured and dimensioned to fit over the ETT without contacting it. At the proximal end of tube 50, a flexible portion 52 is provided. The proximal end of tube 50 above flexible portion 52 is configured for attachment to an ETT holder system, such as tube holder mouthpiece 16. The attachment configuration of the proximal end may comprise a specially configured connector or collar, or the tube may simply terminate with a smooth edge adapted to contact mouthpiece 16. Movement sensor 58 may be positioned also in the region of flexible portion 52 in order to detect motion of tube 50 resulting from patient touches or attempts at removal as described further below. Flexible portion 52 allows tube 50 to be moved slightly side-to-side, or pulled distally, without imparting any motion to the ETT itself. This can be critical for avoiding dislodgment of the ETT, which can happen from even very small movements depending on the patient and clinical situation. Movements of inch and potentially less can be sufficient to dislodge the ETT, leading to potentially life threatening complications. Allowing the patient to cause a small amount of motion on the tube guard also may tend to decrease the likelihood of a patient pulling or otherwise handling the tube to the point of causing problematic movement of the ETT by providing a sensation of movement of the device without actually allowing the ETT itself to move.

Another aspect to preventing unintended dislodgement of the ETT is the attachment to the holder and the holder system itself. In some embodiments, the proximal end of tube 50 may include attachment means for securing it to a conventional ETT tube holder mouthpiece 16. Such attachment means may comprise appropriate attachment openings or connection points (such as rigid connection point 62a and flexible connection point 62b) in tube 50 such that rigid strap 60a and flexible strap 60b may be used to secure the tube to the holder. In such an arrangement, rigid strap 60a may be secured at the proximal end of tube 50 and flexible strap 60b secured somewhat more distally, below flexible portion 52. In another alternative, openings along the proximal end of tube 50 may be used to secure the tube to the holder via zip ties or other commonly used attachment devices. In such a manner guard tube 50 may be utilized with a wide variety of different holder systems without the need for a specifically adapted system such as explained in more detail below.

Elongated openings 54 on sides of tube 50 allow for ports and attachments such as port 28 or bronchoscopy port 32 (depending on location) to extend through tube guard 50. The elongated shape of openings 54 allows for motion of tube 50 when flexible portion 52 is extended due to patient contact with the tube.

Figure 3A:
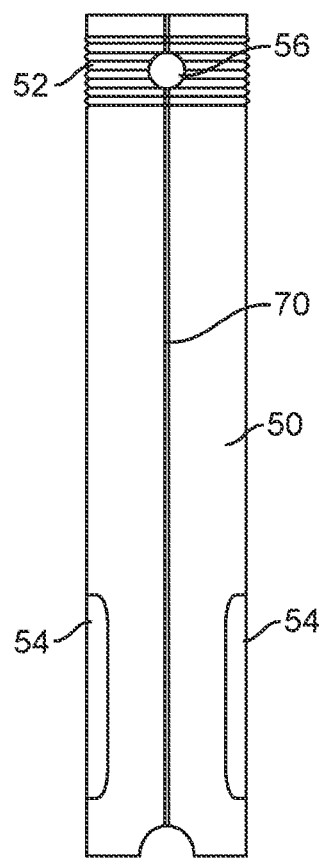
FIGS. 3A, 3B and 3C are an elevation view and two end views of alternative ETT guard tubes according to embodiments disclosed herein.
Figure 3B:
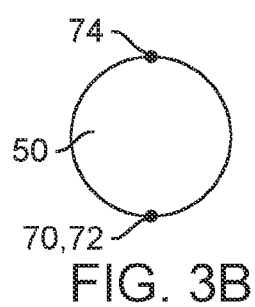
Figure 3C:
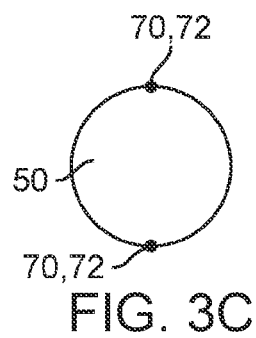
Figure 4:
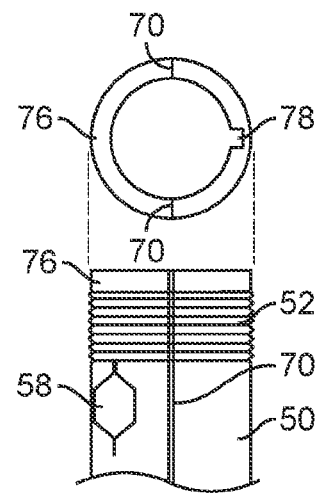
FIG. 4. is a side and end view of a further alternative ETT guard tube with a connection ring for connecting to a ETT holder.
Figure 5A:
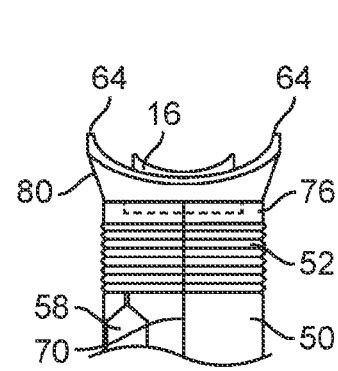
FIGS. 5A and 5B are side views illustrating connection and separation, respectively, of an ETT guard tube and ETT holder in one alternative embodiment.
Figure 5B:
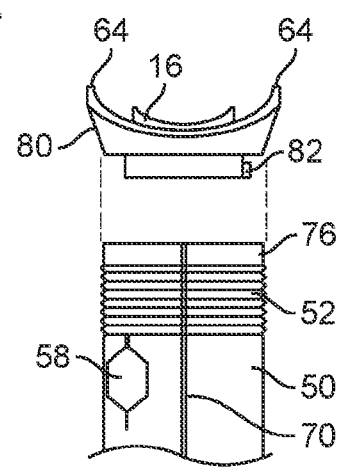
Figure 6:
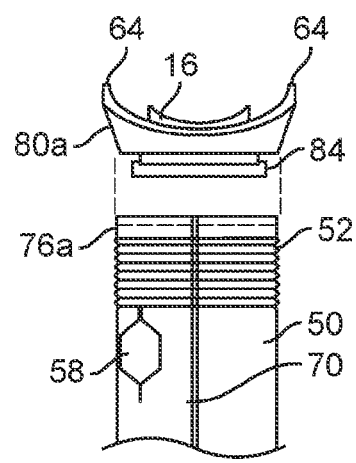
FIG. 6 is a side view showing an alternative ETT guard tube and ETT holder in a disconnected state.
Figure 7:
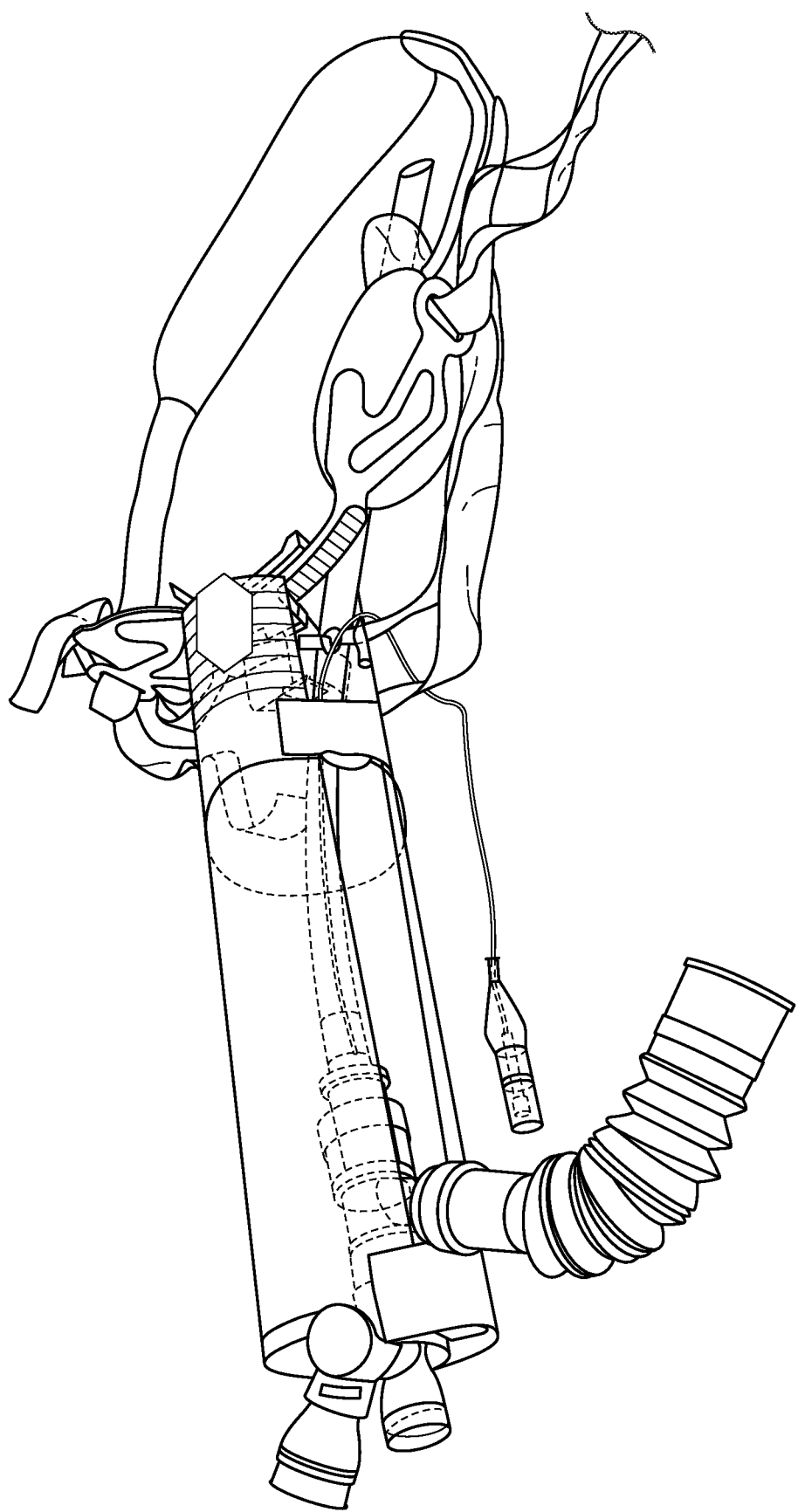
FIG. 7 is a photograph of the ETT guard over an ETT/ETT holder system/ventilator connector system in a side view.

In order to allow tube 50 to be installed and removed without removing the ETT, at least one parting line 70 is provided, extending along the longitudinal extent of the guard tube as shown, for example, in FIG. 3A. In one alternative, a single parting line 70 is provided on one side of tube 50 and longitudinal hinge 74 provided opposite, as shown in FIG. 3B. In this embodiment, a single connector 72 runs along parting line 70 and tube 50 opens along hinge 74. Detent connector 72 may comprise interfering/interlocking longitudinal ridges that lock together under sufficient finger pressure and then may be removed by appropriate finger pressure adjacent the joined edges to snap the edges apart, something easily accomplished by healthcare personnel, but not by a typical, intubate patient. In some embodiments, two parting lines 70 may be provided, one on each side of the tube. When two parting lines 70 are provided, they may both be fitted with connectors such as interlocking ridges 72, which then allow the two parted halves of tube 50 to be pushed and locked together and then parted by separating the connectors with appropriate finger pressure. Rather than being continuous along the length, both connection 72 and hinge 74 may alternately be provided as one or more shorter connectors and hinges, respectively.

Also shown in FIG. 3A is optional nasogastric tube opening 56. Opening 56 permits a second, smaller patient access tube such as a nasogastric tube to be placed within guard tube 50. By locating opening 56 along parting line 70, the guard tube may be placed or removed without removing or detaching the nasogastric tube. Also, the nasogastric tube may be later added to guard tube 50 without disturbing the ETT therein.

Alternative means for attaching tube 50 with the holder mouthpiece are shown, for example, in FIGS. 4, 5A, 5B and 6. In embodiment, attachment collar 76 is provided at the proximal end of tube 50, proximally with respect to flexible portion 52. Attachment collar 76 may have a notch and groove to form keyway 78. In one alternative holder mouth piece 80, shown in FIGS. 5A and 5B, a protrusion sized to be received within the opening of attachment collar 76 is provided with extending key 82. To connect the two parts, tube 50 and attachment collar 76 are placed over the mouthpiece and rotated to lock it in place via key 82 and keyway 78. In another alternative embodiment, attachment collar 76a (FIG. 6) is provided with an annular groove on the inside surface. This annular groove is sized to receive annular protrusion 84 on alternative mouthpiece 80a when tube 50 is opened and closed along parting line(s) 70.

Sensor 58, as shown, for example in FIG. 2, may take a variety of forms. It may be a motion sensor that simply detects motion of tube 50 when exceeding predetermined threshold levels or it may be a strain gauge-type sensor that detects changes in length of flexible portion 52, also with set threshold, if desired. Sensor 58 may be connected with the patient's monitoring system and send an alarm to attending personnel when thresholds of movement or elongation are exceeded. This provides an immediate alert of any movement, which may thus prevent unintended dislodgement of the ETT.

Figure 8:
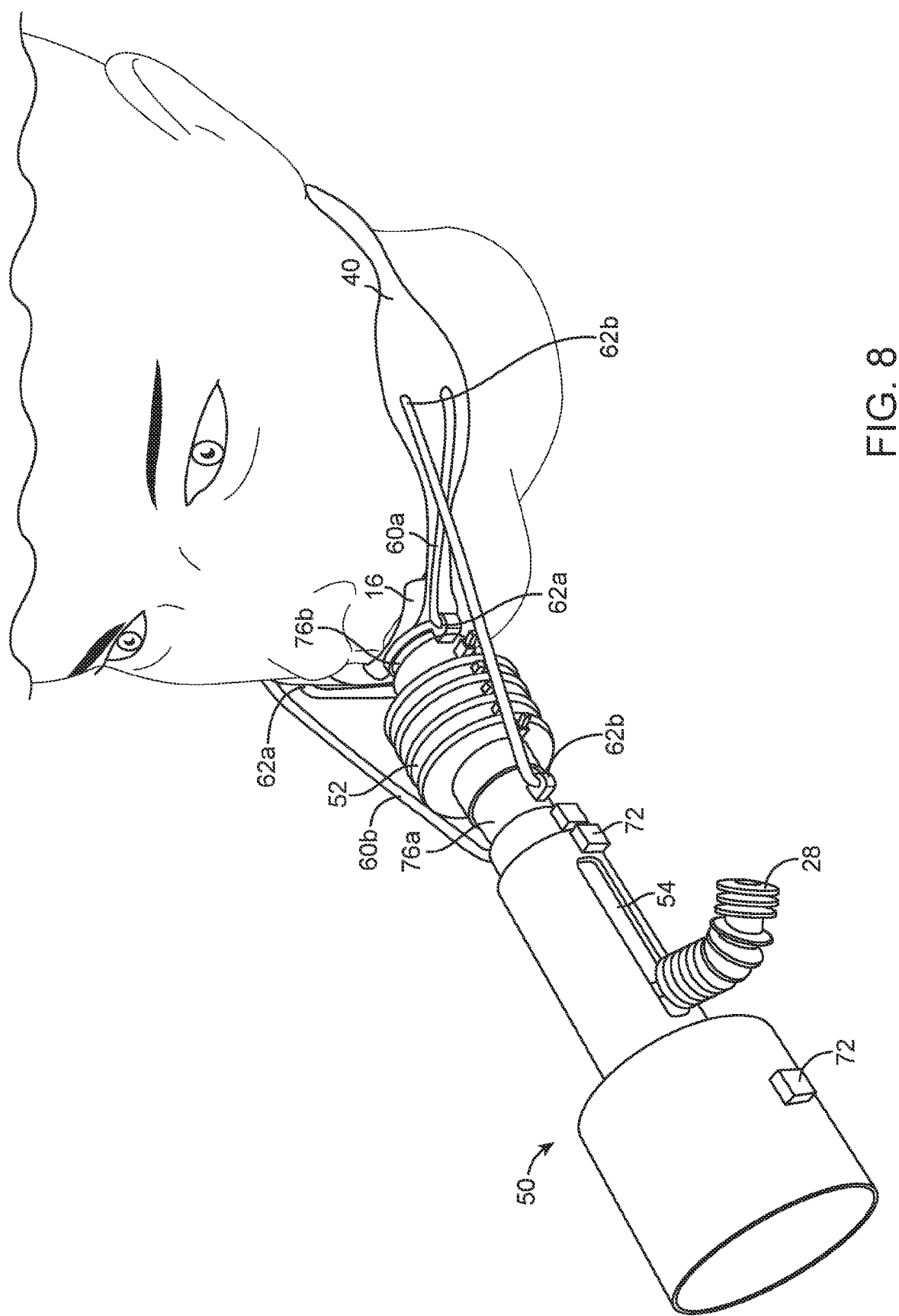
Figure 9:
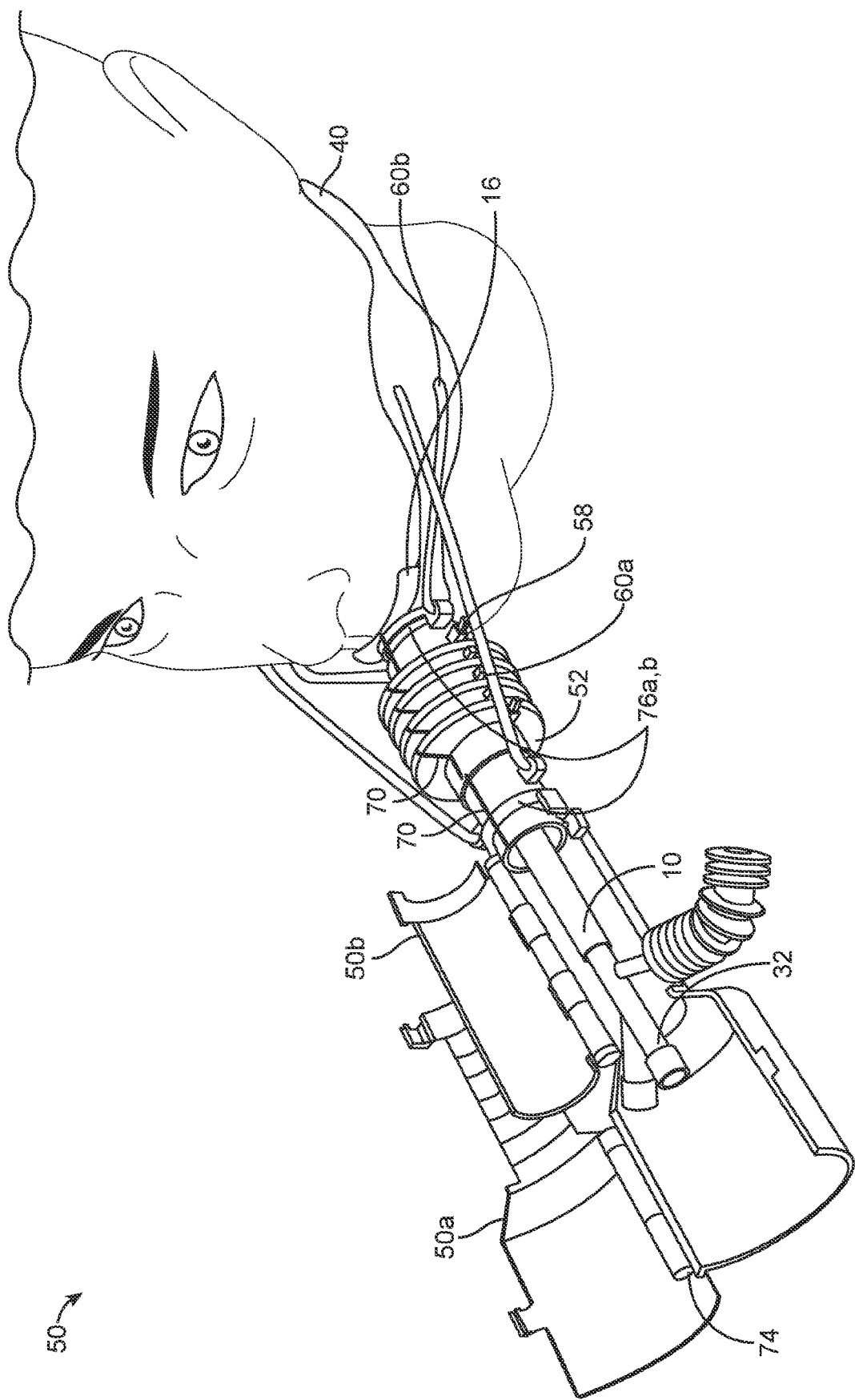

A further alternative embodiment of a tube guard is shown in FIGS. 8 and 9. In this embodiment, tube 50 forms an elongate tube structure made in two telescoping parts 50a and 50b. Both tube parts include hinges 74 and closure elements 72. Proximal tube part 50b is adapted to connect with a distal collar 76a using an annular ring connector such as annular protrusion 84 in FIG. 6. Flexible portion 52 is proximally connected to distal collar 76a and proximal collar 76b connects flexible portion 52 to tube holder mouthpiece 16. In this embodiment, flexible straps 60a are connected to distal collar 76a and rigid straps 60b are connected to proximal collar 76b.

Distal part 50a of telescoping tube 50 has a large distal end to accommodate connector ports and a smaller proximal end with ridges compatible with ridges on inner, proximal tube part 50b in order to provide an adjustable length to accommodate different length ETTs and other intubation devices. Inner, proximal tube part 50b has corresponding ridges to interface with the ridges on tube part 50a. Elongate side ports 54 are provide through both tube parts.

Disclosed tube guards may be used alone or in conjunction with the Protective and Exercise Hand Restraint System as described in Applicant's concurrently filed PCT Application No. PCT/US 18/64618, which is incorporated herein in its entirety, or with other currently marketed mitt restraints as a method of preventing or adding hindrance to self-extubation. In another alternative embodiment, a protective guard system for orally or nasally placed patient access tubes comprises an elongate tubular structure configured and dimensioned to surround an orally or nasally placed patient access tube with a distal end configured to engage a mouthpiece of a tube holder securing the placed tube in the patient's mouth. The elongate tubular structure has a flexible portion and a substantially rigid portion. The substantially rigid portion defines at least one longitudinally extending opening configured and dimensioned to receive a port or connector. The elongate tubular structure is further configured to be opened for lateral placement around or removal from the placed access tube without dislodging the placed access tube from its position in the patient or disconnecting the placed tube from connected devices.

The disclosed system provides unique features that prevent self-extubation while not strapped to a bed or chair for an awake and at-risk patient who might otherwise intentionally or unintentionally self-extubate, and encourage early mobilization and exercise promoting the strength required for advancement from the ventilator. The increased freedom provided by the disclosed system allows for reduced patient agitation and therefore sedation medication may be decreased and minimized which in turn promotes increased patient cognition and thereby would be more likely to reduce the incidence of delirium and PICS. Once the ETT guard is in place, direct nurse or sitter monitoring may not be necessary whereas the absence of restraints to tether a patient to a bed or chair without constant 1:1 supervision invites self-extubation.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure

What is claimed is:

1. A protective guard system for placed patient access tubes, comprising:
    an elongate tubular structure configured and dimensioned to surround a place patient access tube with space between the placed tube and the surrounding tubular structure, said tubular structure having length at least substantially equal to the length of the placed tube extending from the patient's mouth and a distal end configured to engage a mouthpiece of a tube holder securing the placed tube in the patient's mouth, wherein:
    said elongate tubular structure has a flexible portion and a substantially rigid portion;
    said substantially rigid portion defines at least one longitudinally extending opening configured and dimensioned to receive a port or connector of the placed tube therethrough and sized to permit movement of the substantially rigid portion without interfering with operation of the port or connector; and
    said elongate tubular structure is further configured to be opened for lateral placement around or removal from the placed access tube without dislodging the placed access tube from its position in the patient or disconnecting the placed tube from connected devices;
    wherein said flexible portion is configured and dimensioned to provide for at least expansion and contraction in a longitudinal direction, with a distal end configured to mate with the mouthpiece of the tube holder and a proximal end mating with the substantially rigid portion.

2. The protective guard system of claim 1, further comprising a motion sensor mounted with the elongate tubular structure, said motion sensor configured to detect movement of the system exceeding a predetermined motion threshold.

3. The protective guard system of claim 2, wherein said motion sensor comprises a sensor configured to detect elongation of the flexible portion.

4. The protective guard system of claim 1, wherein said elongate tubular structure has a longitudinally extending parting line provided with locking means and an opposed extending hinge structure such that said elongate tubular structure may be opened to be removed and replaced from the placed access tube.

5. The protective guard system of claim 1, wherein said elongate tubular structure has at least two opposed longitudinally extending parting lines, each said parting line provided with locking means such that said elongate tubular structure may separate into at least two parts to be removed and replaced from the placed access tube.

6. The protective guard system of claim 1, wherein said substantially rigid portion comprises a telescoping structure for longitudinal length adjustment.

7. The protective guard system of claim 1, wherein said elongate tube structure further comprises a proximal attachment collar disposed between said substantially rigid portion and said flexible portion, and a distal attachment collar at the distal end of the flexible portion wherein said distal attachment collar is configured to engage the mouthpiece of the tube holder.

8. The protective guard system of claim 7, wherein said flexible portion and said substantially rigid portion are separately formed and removable and attachable at said proximal attachment collar.

9. The protective guard system of claim 1, further comprising:
- fixed connection points positioned on substantially opposite sides and distally of or on a distal aspect of the flexible portion;
- longitudinally inextensible connection straps attachable between each said fixed connection point and adapted to be attached to a head strap of the tube holder;
- moveable connection points positioned on substantially opposite sides and proximally of or on a proximal aspect of the flexible portion; and
- longitudinally extensible connection straps attachable between each said proximal connection point and adapted to be attached to the head strap of the tube holder.

10. The protective guard system of claim 9, wherein said connector comprises attachment collar disposed around the distal end of the flexible portion and a mating attachment portion on the tube holder mouthpiece.

11. The protective guard system of claim 10, wherein one of said flexible portion attachment collar and said mating attachment portion comprises a key and one of a mating keyway such that the elongate tube structure may be mated with the tube holder mouthpiece and rotated to lock the said structure to said mouthpiece.

12. The protective guard system of claim 10, wherein said flexible portion attachment collar and said mating attachment portion together comprise a mating annular ring and annular recess such that the elongate tube structure may be mated with the tube holder mouthpiece by opening the elongate tubular structure to engage said annular ring and annular recess.

13. The protective guard system of claim 1, further comprising:
- a tube holder including a tube holder mouthpiece; and
- a connector adapted to mate with the tube holder mouthpiece disposed at the distal end of the flexible portion.

14. The protective guard system of claim 1, wherein said flexible portion of the elongate tubular structure defines an opening disposed to be opened with the elongate tubular structure and configured to receive a nasal access tube therethrough.

* * * * *